United States Patent [19]
Ley et al.

[11] Patent Number: 6,039,939
[45] Date of Patent: Mar. 21, 2000

[54] N-ACYL-HYDROXYAMINO ACID ESTERS AND THEIR USE

[75] Inventors: Jakob Ley, Holzminden; Roland Langner, Bevern, both of Germany

[73] Assignee: Haarmann & Reimer GmbH, Germany

[21] Appl. No.: 09/039,055

[22] Filed: Mar. 13, 1998

[30] Foreign Application Priority Data

Mar. 14, 1997 [DE] Germany .......................... 197 10 612

[51] Int. Cl.$^7$ .................................................. A61V 31/74
[52] U.S. Cl. ..................... 424/78.03; 424/70.1; 514/423; 548/533
[58] Field of Search ........................... 548/533; 514/423; 424/78.03, 70.1

[56] References Cited

U.S. PATENT DOCUMENTS 4,016,287   4/1977   Eberhardt et al. ...................... 424/309

FOREIGN PATENT DOCUMENTS

| 44 03 258 C1 | 3/1995 | European Pat. Off. . |
| 4420736C1 | 6/1993 | Germany . |
| 44 20 736 C1 | 6/1994 | Germany . |
| 1246141 | 8/1968 | United Kingdom . |

WO 94/07844   4/1994   WIPO .

OTHER PUBLICATIONS

De Paepe, K. et al., Ceramides/Cholesterol/Free fatty acids containing cosmetics: The effect on barrier function, Apr. 1996, pp. 199–200, 202–204.
Watkins, S. et al., Questamide H—A Designed ceramide analogue, Apr. 1995, pp. 228, 231, 234, 236, 238.
Petersen, Ceramides Key Components for Skin Protection, Feb. 1992, pp. 45–49.
Imokawa, Water–retaining function in the stratum corneum and its recovery properties by synthetic pseudoceramides, (Sep./Oct. 1989), pp. 273–285.
Casonline Printout 79:5555; RN 42167–59–9, 1973.
Feil and Vercellotti, "Stability of 3–Glycosyloxprolines In An Alkaline Medium. Synthesis Of Model Compounds", *O–Glycosyl Hydroxyprolines*, pp. 311–322 (1973).
Chem Abstracts 1990:513876; rn 129018–15–1 and 129024–28–8.

*Primary Examiner*—Samuel Barts
*Attorney, Agent, or Firm*—Brinks Hofer Gilson & Lione

[57] ABSTRACT

N-Acyl-hydroxyamino acid alkyl esters help to strengthen the natural barrier function of the skin against environmental influences and external irritation. They improve the suppleness and the elasticity of skin and hair, help to increase the moisture content and protect skin and hair from drying out.

3 Claims, No Drawings

N-ACYL-HYDROXYAMINO ACID ESTERS AND THEIR USE

The present invention relates to N-acyl-hydroxyamino acid esters, to a process for their preparation, to hydroxyamino acid esters and their salts which can be used as intermediates for the preparation of these N-acyl-hydroxyamino acid esters, to the use of N-acyl-hydroxyamino acid esters for preparing skin care products and to skin care products containing N-acyl-hydroxyamino acid esters. For the purposes of the invention, skin care products are cosmetic products for protecting and caring for the skin and hair.

The outermost layer of human skin, the horny layer or the stratum corneum, consists of dead corneocytes which are held together by lipids. These lipids are composed of approximately 50% by weight of ceramides, approximately 15% by weight of cholesterol, 5% by weight of cholesteryl esters and 33% by weight of free fatty acids (K. De Paepe et al., SÖFW-Journal 1996, 122 (4), 199–200, 202–204). Ceramides are lipophilic amides of long chain fatty acids which are generally derived from sphingosine or phytosphingosine. The lipid layer and in particular the ceramides play an important role as the water-retaining barrier for the skin and are thus largely responsible for moisture storage in the horny layer. This function is explained by the ability of the ceramides to form double membrane layers, between which water is stored. The external application of ceramides leads to the lipid barrier being restored, meaning that skin damage which is caused by destruction of the same can be repaired (R.D. Petersen, Cosm. Toil. 1992, 107 (2), 45–49).

Since ceramides cannot be readily obtained either synthetically or from natural sources, their availability is limited. There have therefore already been attempts to synthesize ceramide-like structures or synthetic barrier lipids and to use them for skin care (G. Imokawa et al., J. Soc. Cosmet. Chem. 1989, 40, 273–285; S. Watkins et al., SÖFW-Journal 1995, 121 (4), 228–238).

Accordingly, DE-C 44 03 258, for example, proposes alkylamides of the structure

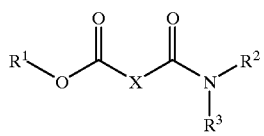

where
R¹ represents a branched alkyl and/or alkenyl radical having 12 to 50 carbon atoms, R² represents hydrogen or an optionally hydroxy-substituted alkyl radical having 1 to 30 carbon atoms, R³ represents a hydroxyalkyl radical having 2 to 12 carbon atoms and 1 to 10 hydroxyl groups or a glycosyl radical, and X represents a linear or branched alkylene radical having 1 to 6 carbon atoms.

WO 94/07 844 discloses amides of the structure

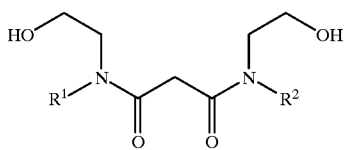

where R¹ and R² represent hydrocarbon radicals.

DE-C 44 20 736 discloses, for skin care, sugar acid derivatives and amino acid derivatives of the formula

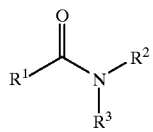

where
R¹CO represents a hydroxyacyl radical having 3 to 8 carbon atoms and 2 to 7 hydroxyl groups and
R² and R³ can be identical or different, and represent hydrogen, a linear or branched alkyl group having 1 to 50 carbon atoms, or together are a group of the formula

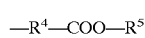

—R⁴—COO—R⁵ where
R⁴ represents an alkylene group having 1 to 18 carbon atoms, which may comprise a further ester group COO—R⁶, where R⁶ is a linear or branched alkyl group having 1 to 50 carbon atoms, and R⁵ is a linear or branched alkyl group having 6 to 50 carbon atoms, with the proviso that at least two of the groups R², R³, R⁵ and R⁶ are long chain radicals having 6 to 50 carbon atoms, or at least one of the groups R², R³, R⁵ and R⁶ is a branched alkyl group, the branches having at least 6 carbon atoms.

Despite these attempts, the success which can be obtained with these substances is not satisfactory.

The object of the present invention was to develop new biomimetic compounds having ceramide-like actions which can be prepared simply and from natural raw materials.

The invention provides N-acyl-hydroxyamino acid esters of the formula

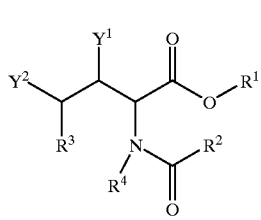

(I)

where
R¹ is a linear, branched or cyclic alkyl or alkenyl group having 5 to 50 carbon atoms and optionally one or more hydroxyl radicals, preferably a linear, branched or cyclic alkyl or alkenyl group having 5 to 24 carbon atoms and optionally 1 to 6 hydroxyl radicals,
R² is a linear or branched alkyl or alkenyl group having 1 to 49 carbon atoms and optionally one or more hydroxyl radicals, preferably a linear or branched alkyl or alkenyl group having 2 to 23 carbon atoms and optionally 1 to 6 hydroxyl radicals, in particular a linear or branched alkyl or alkenyl group having 2 to 23 carbon atoms and optionally 1 to 3 hydroxyl radicals,
Y¹ and Y² are, independently of one another, hydrogen or hydroxyl, and preferably only one of the two groups Y¹ and Y² is a hydroxyl radical and the other is a hydrogen atom,
R³ and R⁴ are either, independently of one another, hydrogen or linear or branched alkyl or alkenyl groups having 1 to 10 carbon atoms, preferably hydrogen or linear or branched alkyl or alkenyl groups having 1 to 4 carbon atoms, in particular hydrogen, methyl or ethyl, especially hydrogen, or $R^3$ and $R^4$ together are an alkylene radical having 1 to 3 carbon atoms, and together with the chain between $R^3$ and $R^4$ form a 5- to 7-membered heterocyclic ring, in which case this alkylene radical can be substituted for its part by 1 to 3 linear or branched alkyl or alkenyl groups or by 1 to 3 hydroxyl radicals, and $R^3$ and $R^4$ together are preferably the alkylene radicals —CH$_2$—, —CH$_2$—CH$_2$—, —CH(OH)—, —CH(OH)—CH$_2$— or —CH$_2$—CH(OH—.

Particular preference is given to N-acyl-hydroxyamino acid esters (I), where $R^1$ and $R^2$ are as defined above and either $R^3$ and $R^4$ are hydrogen atoms and at the same time $Y^1$ and $Y^2$ are, independently of one another, hydrogen atoms or hydroxyl radicals, and in particular $Y^1$ is a hydroxyl radical and $Y^2$ is a hydrogen atom (N-acyl-threonine alkyl ester), or $R^3$ and $R^4$ together are a —CH$_2$—or a —CH(OH)-group, and together with the chain between $R^3$ and $R^4$ form a 5-membered heterocyclic ring, and at the same time $Y^1$ and $Y^2$ are hydrogen atoms or hydroxyl radicals, but in particular $R^3$ and $R^4$ together are a —CH$_2$—group, and together with the chain between $R^3$ and $R^4$ form a 5-membered heterocyclic ring, and one of the two radicals $Y^1$ and $Y^2$ is a hydroxyl radical (N-acyl-hydroxyproline ester).

The N-acyl-hydroxyamino acid esters used for the purposes of the invention strengthen the natural barrier function of the skin and impart a surprisingly positive skin-smoothing and beautifying effect.

The N-acyl-hydroxyamino acid esters according to the invention are colourless or slightly ivory-coloured, odourless substances which can be incorporated homogeneously into the oil phase of cosmetic products.

Particular preference is given to N-acyl-threonine esters and N-acyl-hydroxyproline ester, where $R^1$ is an unbranched alkyl or alkenyl radical having 5 to 24 carbon atoms and $R^2$ is an unbranched alkyl or alkenyl radical having 2 to 23 carbon atoms, as a result of which the amphiphilic compounds can be readily incorporated into the double membrane of the lipid barrier, thus improving the properties of the skin.

The invention also provides a process for preparing the N-acyl-hydroxyamino acid esters (I), according to which a) hydroxyamino acids of the formula

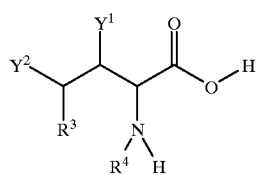

(II)

where $R^3$, $R^4$, $Y^1$ and $Y^2$ are as defined above, or their cationic or anionic salts are esterified with branched or straight-chain alcohols of the formula $R^1$—OH  (III)

where $R^1$ is as defined above, and b) the resulting intermediates of the formula

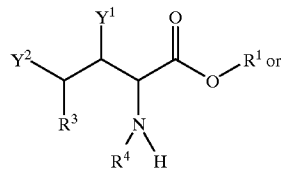

(IV)

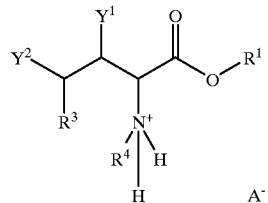

(IVa)

in which $R^1$, $R^3$, $R^4$, $Y^1$ and $Y^2$ are as defined above, and $A^-$ is an inorganic or organic anion, for example halide, sulphate, phosphate, acetate or p-toluenesulphonate anion, are condensed with compounds of the formula $R^2$—COX$^1$  (V), where $R^2$ is as defined above and $X^1$ is a hydroxyl group, a halogen atom, a heterocyclic group (optionally with a fused-on C$_5$–C$_{12}$-aromatic component) having 5 to 6 ring atoms, up to 3 of which can be heteroatoms (up to 1 sulphur atom, up to 2 oxygen atoms and up to 3 nitrogen atoms), C$_6$–C$_{12}$-arylsulphonyl, an —O—X$^2$ group or —S—X$^2$ group, where X$^2$ is a C$_1$–C$_{10}$-alkyl or C$_2$–C$_{10}$-alkenyl group, a C$_6$–C$_{12}$-aryl group, a heterocyclic group (as above), C$_6$–C$_{12}$-arylsulphonyl, an amino group or an R$^2$—CO—group, preferably a hydroxyl group, a halogen atom or an —O—X$^2$ or —S—X$^2$ group, where X$^2$ is a nitro-substituted C$_6$–C$_{12}$-aryl group, C$_6$–C$_{12}$-arylsulphonyl or a cyclic secondary C$_4$–C$_{10}$-amino group, but in particular is a hydroxyl group, chlorine, bromine, an —O—X$^2$ or —S—X$^2$ group, where X$^2$ is p- or o-nitrophenyl, p-toluenesulphonyl, N-benzotriazolyl or N-succinimidyl.

Suitable starting compounds for preparing the N-acyl-hydroxyamino acid esters according to the invention are the hydroxyamino acids (II), preferably the naturally occurring or synthetic threonines and hydroxyprolines (L-, D- or D,L-, in the form of all diastereomers). In particular, L-threonine, which is widespread in nature, and trans-4-hydroxy-L-proline, which occurs in natural collagen and also in plants, are used.

Particularly suitable alcohols (III) are linear primary, branched primary and secondary cycloaliphatic alcohols. Examples of linear alcohols are the natural vegetable fatty alcohols, such as, for example, lauryl alcohol, myristyl alcohol, cetyl alcohol, stearyl alcohol, behenyl alcohol, oleyl alcohol, elaidyl alcohol, ricinoleyl alcohol, linoleyl alcohol, linolenyl alcohol and their technical-grade mixtures.

Examples of secondary cycloaliphatic alcohols are the naturally occurring or synthetic alcohols (−)-menthol or (+)-menthol.

The intermediates (IV) and (IVa) can be synthesized by esterification of the aforementioned hydroxyamino acids (II) with the aforementioned alcohols (III) in a manner known per se in the alcohol (III) with or without solvent by addition of a con(1ensation-promoting compound. The reaction is preferably carried out in the alcohol (III) with the addition of dry hydrogen chloride gas or thionyl chloride at, preferably, from 10 to 150° C. Typical reaction times are between 0.5 and 24 hours. Alternatively, the reaction can be carried out in an organic solvent which forms an azeotrope with water, with the addition of an acid. Preferably, aromatic solvents, in particular benzene, toluene or xylene, with the addition of strong acids, in particular sulphuric acid and aromatic sulphonic acids, are used in the boiling heat and the water of reaction is removed by azeotropic means.

Particular novelties are the esterification of hydroxyprolines and threonines with primary alcohols having 5 or more carbon atoms, and the isolation and purification of the compounds (IV) and (IVa) by crystallization, recrystallization, for example from lower ketones, or by liquid chromatography.

Surprisingly, it has been found that the intermediate products (IV) and (IVa), particularly the hydroxyproline esters and their ammonium salts, display an antimicrobial action towards bacteria which settle on the skin, in particular towards Corynebacterium, Aspergillus, Pseudomonas and Staphylococcus species, in particular towards Corynebacterium xerosis, Aspergillus niger, Pseudomonas aeruginosa and Staphylococcus aureus.

Particularly suitable acylation agents (V) are linear and branched primary activated carboxylic acid derivatives. Preference is given to using fatty acid halides or the active esters of fatty acids, in particular the o- or p-nitrophenyl esters or the N-succinimidyl esters, which can all be prepared in a known manner from the carboxylic acids by halogenation or esterification. Examples of linear primary carboxylic acids are the natural fatty acids capric acid, lauric acid, myristic acid, palmitic acid, stearic acid, arachidic acid, behenic acid, erucic acid, palmitoleic acid, oleic acid, petroselic acid, elaidic acid, linoleic acid, α-linolenic acid, γ-linolenic acid and arachidonic acid and their technical-grade mixtures, and the natural hydroxy fatty acids cerebronic acid (2-hydroxytetracosanic acid), α-hydroxynervonic acid (2-hydroxy-15-Z-tetracosenoic acid) and ricinoleic acid.

The N-acyl-hydroxyamino acid esters (I) according to the invention can be prepared by reacting the intermediates (IV) and (IVa) with an acylation agent (V). The reaction is preferably carried out in a solvent with the addition of acid scavengers. In particular, the acylation is carried out in water or a water/solvent mixture with fatty acid halides or fatty acid esters of N-hydroxysuccinimide in the presence of an acid scavenger or a base. The acid scavenger or base used can be a metal carbonate or metal hydrogencarbonate of main groups 1 to 3, such as, for example, sodium hydrogencarbonate, a tertiary amine, such as, for example, triethylamine, or a heterocycle, such as, for example, pyridine. Subsequently, the products can be purified by distillation, recrystallization, for example from lower alcohols, or liquid chromatography.

The N-acyl-hydroxyamino acid esters (I) can be present in skin care products in quantities of from 0.1 to 50, preferably from 0.1 to 10, in particular from 0.1 to 5, % by weight, based on the total weight of the formulation, and can be in the form of both "water-in-oil" and "oil-in-water" emulsions; other usual auxiliaries and additives can be present in quantities of from 5 to 95, preferably from 10 to 95, % by weight, based on the total weight of the formulation. In addition, the formulations can contain water in a quantity up to 99% by weight, preferably from 5 to 90% by weight, based on the total weight of the formulation.

In a preferred embodiment of the invention, the N-acyl-hydroxyamino acid esters according to the invention can be mixed with ceramides, other fatty acid amides, cholesterol, cholesterol fatty acid esters, fatty acids, triglycerides, cerebrosides, phospholipids and similar substances, possibly with the formation of liposomes.

Finally, in another embodiment, the N-acyl-hydroxyamino acid esters according to the invention can also be dissolved in squalene or squalane, and optionally formulated with other ingredients together with volatile or non-volatile silicone compounds as anhydrous or almost anhydrous systems.

The N-acyl-hydroxyamino acid esters which can be used as synthetic barrier lipids according to the invention help to strengthen the natural barrier function of the skin against environmental influences and external irritation. They improve the suppleness and elasticity of skin and hair, help to increase the moisture content and prevent skin and hair from drying out.

Therefore, the invention further provides for the use of the N-acyl-hydroxyamino acid esters (I) as synthetic barrier lipids for preparing skin care products in the narrower sense, in which they may be present in quantities of from 0.1 to 50, preferably 0.1 to 10, in particular from 0.1 to 5, % by weight, based on the total weight of the skin care products, and for preparing hair care products in which they can be present in quantities of from 0.1 to 15, preferably from 0.1 to 5, in particular from 0.1 to 2, % by weight, based on the total weight of the hair care product. Typical examples are skin creams, soft creams, nourishing creams, sunscreens, night creains, skin oils, beauty lotions, body aerosols, hair shampoos, hair rinses, hair treatments, hair sprays and hair lotions.

EXAMPLES trans-4-Hydroxy-L-proline 1-dodecyl ester hydrochloride

Thionyl chloride (15.5 g, 130 mmol) at 25 to 30° C. was added with stirring to 1-dodecanol (190 g, 1.02 mol). After adding trans-4-hydroxy-L-proline (15 g, 114.4 mol), the suspension was stirred for 5 hours at 100° C. The 1-dodecanol was distilled off under reduced pressure from the now clear reaction solution, and the cooled crystalline residue was dissolved in methanol and filtered. The solvent was distilled off under reduced pressure and distillation was interrupted when crystallization started. The residue was precipitated from diethyl ether, then the precipitate was filtered off and washed with diethyl ether. Yield: 35.3 g (105.1 mmol, 92% of theory) of a white crystalline powder. $^1$H-NMR (CD$_3$SOCD$_3$)δ=0.86 (3H, t), 1.25 (18H, m), 1.61 (2H, m), 2.08 (1H, m), 2.18 (1H, m), 3.06 to 3.3 (partly under H$_2$O signal, m), 4.16 (2H, m) 4.45 (2H, m), 5.53 (1H, m), 9.5 to 10 ppm (2H, broad); $^{13}$C-NMR (CD$_3$SOCD$_3$)δ= 168.8 (s), 68.4 (d), 65.8 (t), 57.4 (d), 53.2 (d), 37.0(t), 31.2 (t), 28.94 (t), 28.90 (t), 28.86 (t), 28.81 (t), 28.60 (t), 28.51 (t), 27.8 (t), 25.08(t) 22.0 (t), 13.9 ppm (q). MS (ESI) m/e=300.1 (M+of the cation).

The following compounds were obtained in analogous manner as white or amber-coloured crystalline powders:

trans-4-hydroxy-L-proline 1-hexyl ester hydrochloride trans-4-hydroxy-L-proline 1-heptyl ester hydrochloride trans-4-hydroxy-L-proline 1-octyl ester hydrochloride trans-4-hydroxy-L-proline 1-nonyl ester hydrochloride trans-4-hydroxy-L-proline 1-decyl ester hydrochloride trans-4-hydroxy-L-proline 1-tetradecyl ester hydrochloride trans-4-hydroxy-L-proline 1-hexadecyl ester hydrochloride.

L-Threonine dodecyl ester

L-Threonine (2.6 g, 21.8 mmol), 1-dodecanol (5.18 g, 27.23 mmol) and p-toluenesulphonic acid monohydrate (4.10 g, 22 mmol) were refluxed in benzene (80 ml) in a Dean Stark water separator for 16 hours. The mixture was then diluted with 100 ml of toluene, and the organic phase was washed with water and sat. aqueous sodium chloride solution, dried over $Na_2SO_4$ and filtered, and the filtrate was concentrated by evaporation under reduced pressure. The colourless oil was dried at 0.2 mbar for 1 hour. Yield: 8 g. $^1$H-NMR (CDCl$_3$)δ=0.87 (3H, t), 1.24 (3H, d), 1.24 to 1.40 (18H, m), 1.60 to 1.70 (2H, m), 3.25 (1H, d), 3.84 (1H, m), 4.13 ppm (2H, m); $^{13}$C-NMR (CDCl$_3$)δ=174.2 (s), 68.3 (d), 65.5 (t), 60.0 (d), 31.9 (t), 29.7 (2C, t), 29.6 (t), 29.5 (t), 29.4 (t), 29.2 (t), 28.6 (t), 25.9 (t), 22.7 (t), 19.8 (q), 14.1 ppm (q).

The following compound was obtained in an analogous manner as a colourless oil: L-threonine decyl ester.

N-(1-Hexadecanoyl)-trans-4-hydroxy-L-proline 1-dodecyl ester trans-4-Hydroxy-L-proline dodecyl ester hydrochloride (10 g, 29.8 mmol) was dissolved in 1,4-dioxane (125 ml) and water (125 ml); with stirring, sodium hydrogencarbonate (10.4 g, 123.8 mmol) was firstly added, followed by 1-hexadecanoyl chloride (9 ml, 8.19 g, 29.8 mmol). The reaction mixture was stirred for 1 hour at room temperature. The suspension was adjusted to pH 1 to 1.5 and then filtered. The residue was washed with water until neutral and dried under reduced pressure in the melt. Yield: 15.1 g (28 mmol, 94% of theory, 97 to 100% purity [HFLC]) of a white waxy crystalline mass, m.p.: 39 to 44° C. $^1$H-NMR (CDCl$_3$)δ=0.89 (6H, t), 1.2 to 1.4 (40H, m), 1.5 to 1.7 (61–1, m), 2.05 to 2.40 (4H, dm), 3.79 (1H, dd), 4.12 (2H, m), 4.5 to 4.6 ppm (2H, m); $^{13}$C-NMR (CDCl$_3$)δ=172.50 (s), 172.48 (s), 70.4 (d), 65.4 (t), 57.6 (d), 55.1 (t), 37.9 (t), 34.6 (t), 32.0, 29.72 (2C), 29.70 (2C), 29.68 (4C), 29.66, 29.62, 29.56 (2C), 29.48, 29.40, 29.38 (2C,), 29.28, 28.56, 25.85, 24.68, 22.70 (2C), 14.1 (2C, q,q). Elemental analysis: calc.: C 73.7%, H 11.8%, N 2.6%, O 11.9%; found: C 73.5%, H 11.8%, N 2.5%, O 12.2%.

The following compounds were obtained in analogous manner in the form of colourless oils or colourless waxy substances:

N-(1-decanoyl)-trans-4-hydroxy-L-proline 1-dodecyl ester: m.p. <20° C.

N-(1-dodecanoyl)-trans-4-hydroxy-L-proline 1-dodecyl ester: m.p. 20–25° C.

N-(1-tetradecanoyl)-trans-4-hydroxy-L-proline 1-dodecyl ester: m.p. 32–39° C.

N-(1-tetradecanoyl)-trans-4-hydroxy-L-proline 1-tetradecyl ester: m.p. 40–45° C.

N-(1-dodecanoyl)-trans-4-hydroxy-L-proline 1-tetradecyl ester: m.p. 35–40° C.

N-(1-octadecanoyl)-trans-4-hydroxy-L-proline 1-hexadecyl ester: m.p. 40–50° C.

N-Dodecanoyl-L-threonine dodecyl ester

The L-threonine dodecyl ester (8.8 g) was dissolved in 1,4-dioxane (60 ml) and water (50 ml), and sodium hydrogencarbonate (3 g, 35.7 mmol) and N-succinimidyl laurate (6.48 g, 21.8 mmol) were added. The cloudy mixture was refluxed at approximately 90° C. for 1 hour and then left to cool. At 50° C., the mixture was adjusted to pH 2–3 using 10% HCl and cooled to 15 to 20° C. in an ice bath. At approximately 40° C. the product begins to precipitate out. The crude product is filtered off, washed with water and recrystallized from methanol. Yield: 7.75 g (16.5 mmol, 78% over 2 steps) of colourless crystalline needles (HPLC>99%). m.p.: 97–98° C., $^1$H-NMR (CDCl$_3$)δ=0.86 to 0.90 (6H, mn), 1.23 (3H, d, 6.4 Hz), 1.24 to 134 (34H, m), 1.60 to 1.70(4H, m), 2.00 (1H, d, 5.8 Hz), 2.43 (2H, dd, 2*7.4 Hz), 4.16 (2H, t, 6.8 Hz), 4.30 to 4.37 (1H, m), 4.61 (1H, dd, 8.8 Hz, 2.6 Hz), 6.15 ppm (1H, d, 8.8 Hz); $^{13}$C-NMR (CDCl$_3$)δ=173.7 (s), 171.3 (s), 68.3 (d), 65.9 (t), 57.0 (d), 36.7 (t), 31.9 (2C, t), 29.7 (2C, t), 29.6 (5C, t), 29.5 (t), 29.4 (2C, t), 29.3 (t), 29.2 (t), 28.5 (t), 25.8(t), 25.7 (t), 22.7 (2C, t), 20.0 (q), 14.1 ppm (2C, q); elemental analysis: calc.: C 71.6%, H 11.8%, N 3.0%, O 13.6%; found: C 71.8%, H 11.2%, N 2.9%, O 13.5%.

The following compound was obtained in analogous manner in the form of colourless waxy crystals:

N-(1-decanoyl)-L-threonine 1-decyl ester.

"Oil-in-water" emulsion formulation example

| Part | Starting materials name (Manufacturer) | Chemical name | Content in % by wt |
|---|---|---|---|
| A | Arlatone 983 S ® (ICI) | Ether of polyethylene glycol with glyceryl monostearate | 1.20 |
| | Brij 76 ® (ICI) | 3,6,9,12,15,18,21,24,27,30, 33,36-decaoxaoctatetracontan-1-ol | 1.20 |
| | Cutina MD ® (Henkel KGaA) | Glyceryl monostearate | 3.50 |
| | Baysilone oil M10 ® (Bayer) | Polydimethylsiloxane | 0.80 |
| | Eutanol G ® (Henkel KGaA) | 2-Octyldodecanol | 3.00 |
| | Paraffin oil 65cp (Henry Lamotte) | Mineral oil | 8.00 |
| | N-(1-Hexadecanoyl)-trans-4-hydroxy-L-proline 1-dodecyl ester | | 1.00 |
| B | Water, dist. | | 51.30 |
| | Phenonip ® (Nipa Laboratorien GmbH) | 2-Phenoxyethanol and methyl 4-hydroxybenzoate and ethyl 4-hydroxybenzoate and propyl 4-hydroxybenzoate and butyl 4-hydroxybenzoate | 0.50 |
| | Propylene glycol | | 2.00 |
| C | Water, dist. | | 25.00 |
| | Carbopol 2050 ® (B. F. Goodrich Chemical) | Carbomer (CA name) | 0.40 |
| | Aqueous sodium hydroxide solution, 10% | | 1.90 |
| D | Perfume oil | | 0.20 |

Part A is heated to 90° C. Part B is heated to 90° C. and added to part A. Part C: Carbopol is left to swell in water and neutralized. Part C is added at approximately 60° C. to part A/B. Part D is added to part A/B/C at room temperature.

We claim:
1. N-Acyl-hydroxyamino acid esters of the formula

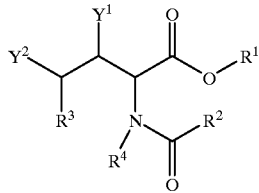
(I)

where $R^1$ is a linear, branched or cyclic alkyl or alkenyl group having 5 to 50 carbon atoms and optionally one or more hydroxyl radicals, $R^2$ is a linear or branched alkyl or alkenyl group having 1 to 49 carbon atoms and optionally one or more hydroxyl radicals, $Y^1$ and $Y^2$ are, independently of one another, hydrogen or hydroxyl, and $R^3$ and $R^4$ together are a —$CH_2$— or a —CH(OH)-group, and together with the chain between $R^3$ and $R^4$ form a 5-membered heterocyclic ring.

2. The compound according to claim 1 where $R^1$ is an unbranched alkyl or alkenyl radical having 5 to 24 carbon atoms, and $R^2$ is an unbranched alkyl or alkenyl radical having 2 to 23 carbon atoms.

3. A cosmetic composition comprising:
the compound of claim 1, and
a carrier.

* * * * *

UNITED STATES PATENT AND TRADEMARK OFFICE
CERTIFICATE OF CORRECTION

PATENT NO. : 6,039,939
DATED : March 21, 2000
INVENTOR(S) : Jakob Ley et al.

It is certified that error appears in the above-identified patent and that said Letters Patent is hereby corrected as shown below:

Title page,
Column 1,
After line 1, under "FOREIGN PATENT DOCUMENTS", insert the following:
-- 928 608 A2     7/1999     European Pat. Off. --.

Signed and Sealed this

Second Day of October, 2001

Attest:

*Nicholas P. Godici*

NICHOLAS P. GODICI
*Attesting Officer*     *Acting Director of the United States Patent and Trademark Office*